_United States Patent_ [19]

Fancher

[11] 4,225,595
[45] Sep. 30, 1980

[54] PIPERAZINE PHOSPHATES AND PHOSPHONATE INSECTICIDES

[75] Inventor: Llewellyn W. Fancher, Orinda, Calif.

[73] Assignee: Stauffer Chemical Company, Westport, Conn.

[21] Appl. No.: 35,043

[22] Filed: May 1, 1979

[51] Int. Cl.³ .................. A61K 31/495; C07D 295/18; C07D 241/06
[52] U.S. Cl. ...................................... 424/200; 544/337
[58] Field of Search ......................... 544/337; 424/200

[56] References Cited

U.S. PATENT DOCUMENTS

| | | | |
|---|---|---|---|
| 2,959,590 | 11/1960 | Moss | 544/337 |
| 3,449,109 | 6/1969 | Richter | 544/337 |

Primary Examiner—Jose Tovar
Attorney, Agent, or Firm—Joel G. Ackerman

[57] ABSTRACT

Insecticidal or miticidal compounds have the formula

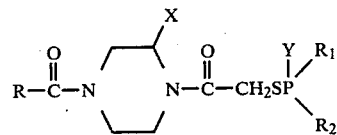

in which
R is selected from the group consisting of 1-4 carbon alkoxy, phenyloxy, and 1-6 carbon alkylthio;
$R_1$ is selected from the group consisting of 1-4 carbon alkyl, and 1-4 carbon alkoxy;
$R_2$ is 1-6 carbon alkoxy;
X is hydrogen or methyl; and
Y is sulfur or oxygen.

49 Claims, No Drawings

PIPERAZINE PHOSPHATES AND PHOSPHONATE INSECTICIDES

This invention relates to novel piperazine phosphate and phosphonate compounds having the formula

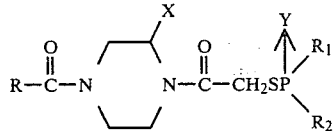

in which

R is selected from the group consisting of 1–4 carbon alkoxy, phenyloxy and 1–6 carbon alkylthio;

$R_1$ is selected from the group consisting of 1–4 carbon alkyl, and 1–4 carbon alkoxy;

$R_2$ is 1–6 carbon alkoxy;

X is hydrogen or methyl; and

Y is sulfur or oxygen. The compounds of this invention have shown utility as insecticides.

In one embodiment $R_1$ is 1–4 carbon alkyl and the compounds are phosphonates. In another embodiment, $R_1$ is 1–4 carbon alkoxy and the compounds are phosphates.

This invention also embodies insecticidal compositions of matter comprised of an "insecticidally effective amount" of a compound described herein and an inert carrier or diluent. An "insecticidally effective amount" is that concentration and application rate necessary to injure or kill a substantial percentage of the treated population.

The invention also relates to the method of controlling or eradicating insects by applying an insecticidally effective amount of a compound as defined herein to the insects or their habitat.

Preparation

The compounds typical of this invention are prepared by a two-step reaction process. The first step involves the chloroacetylation of a mono-substituted piperazine by chloroacetyl chloride or chloroacetic anhydride.

The mono-substituted piperazine intermediate, if not commercially available may be prepared by the reaction of piperazine and an acetyl chloride under basic conditions.

The chloroacetylation reaction is carried out in the presence of a base such as N,N-dimethylaniline and in an inert solvent such as tetrahydrofuran. Temperature ranges, depending on the chloroacetylating agent and the base, range from approximately −30° C. to 100° C.

The substituted chloracetylated piperazine is reacted with a dithiophosphoric or dithiophosphonic acid salt, such as potassium, sodium, or ammonium, which is either performed or formed in situ in the presence of an inert solvent. The product is piperazine phosphate or phosphonate.

The following are selected examples of the preparation of specific compounds. (The compound numbers correlate with the numbers in Table I.)

EXAMPLE 1

(Compound No. 10)

Preparation of 1-N-ethoxycarbo-4-N-O,O-dimethyl phosphorodithioylacetyl piperazine The intermediate 1-N-ethoxycarbo-4-N-chloropiperazine ,3.52 grams (g) or 0.015 mole) was dissolved in 30 milliliters (ml) of tetrahydrofuran. Then 2.69 g (0.017 mole) of dithiophosphoric acid was added. The mixture was cooled to 15° C. With temperatures kept below 25° C., 1.72 g (0.017 mole) of triethylamine was added to the mixture. The reaction was allowed to stand at ambient temperature for over two days.

The solvent was removed under reduced pressure evaporation below 40° C. The residue was taken up in 25 ml of benzene and 50 ml of ether. It was washed twice with 50 ml of water and dried over magnesium sulfate. The product was filtered and vacuum evaporated, leaving 2.87 g (72.5% yield) of a light amber-colored viscous liquid ($n_D^{30}$ 1.5416). The structure was confirmed by nuclear magnetic reasonance (NMR).

EXAMPLE 2

(Compound No. 20)

Preparation of 1-N-isopropoxycarbo-4-N-O,O-diethylphosphoromonothioylacetyl piperazine The intermediate 1-N-isopropoxy piperazine (4.3 g or 0.025 mole) was mixed with 25 ml of tetrahydrofuran. After adding 3.0 g (0.025 mole) of N,N'-dimethylaniline to the mixture, it was cooled below 15° C. and 5.13 g (0.03 mole) chloroacetic anhydride was added with cooling below 25° C. The mixture was allowed to stand for ½ hour. It was then warmed on a steam bath for 5 minutes. The solvent was removed by vacuum evaporation. The residue was taken up in chloroform and washed with water.

The aqueous layer was initially too acidic. Therefore, it was washed with 50 ml of saturated sodium carbonate, followed by two washings with 50 ml of water. The product was dried over magnesium sulfate, filtered, and vacuum evaporated. The product consisted of 6.5 g of chloroacetyl reactant ($n_D^{30}$ 1.5168).

This reactant was combined with 5.82 g (0.028 mole) of O,O-diethyl monothiophosphoric acid potassium salt and 35 ml of acetone. The mixture was refluxed on a steam bath for 4 hours. The solvent was removed by vacuum evaporation. The residue was taken up in chloroform and washed twice with 75 ml of water. It was dried over magnesium sulfate, filtered, and vacuum evaporated. The product was 8.92 g (93% yield) of an amber-colored liquid ($n_D^{30}$ 1.4990). Structure was confirmed by NMR.

EXAMPLE 3

(Compound No. 25)

Preparation of 1-N-methylmercaptocarbo-4-N-ethyl,O-isobutylphosphonodithioylacetyl piperazine The intermediate 1-N-methylmercaptocarbo-4-N-chloroacetyl piperazine was prepared by dissolving 12.8 g (0.08 mole) of 1-N-methylmercaptocarbo piperazine in 40 ml tetrahydrofuran. Then 9.68 g (0.08 mole) N,N'-dimethylaniline was stirred into the mixture. After cooling to 15° C., 17.1 g (0.10 mole) of chloroacetic anhydride was added portion-wise with cooling below 25° C.

The mixture was warmed on a steam bath for five minutes. It was cooled and poured into 100 ml of water containing 25 ml of concentrated hydrogen chloride solution. The product was recovered by two extractions with 100 ml and 50 ml portions of benzene. After washing with 25 ml of dilute sodium chloride, the pH remained at 1. Therefore, it was washed once with 25 ml of saturated sodium bicarbonate and three times with 25 ml saturated sodium chloride. Drying over magnesium sulfate, filtration, and evaporation under reduced pressure followed. The intermediate product was 14.72 g (77.8% yield) of a yellow viscous liquid ($n_D^{30}$ 1.5605). Structure was confirmed by NMR.

A 2.84 g (0.012 mole) portion of the above intermediate was dissolved by warming in 40 ml dry acetone. After cooling the mixture to 15° C., 2.97 g (0.015 mole) of N-ethyl,O-isobutylthioyl phosphonic acid and 1.52 g (0.015 mole) triethylamine were added. The pH was adjusted to 7.5 with a few additional drops of the amine. The mixture was refluxed on a steam bath for 1 hour followed by vacuum evaporation. The residue was taken up in 50 ml of benzene, washed with 75 ml of saturated sodium chloride, dried over magnesium sulfate, filtered, and vacuum evaporated. The 4.61 g of 1-N-methylmercaptocarbo-4-N-ethyl,O-isobutyl phosphonodithioylacetyl piperazine product was a light amber-colored liquid ($n_D^{30}$ 1.5607). Structure was confirmed by NMR.

Other compounds prepared according to these procedures appear in Table I.

TABLE I

PIPERAZINE PHOSPHATES AND PHOSPHONATES

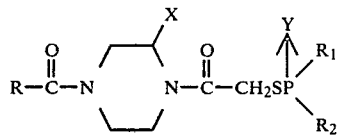

| Compound No. | R | $R_1$ | $R_2$ | X | Y | Chemical Name | Refractive Index |
|---|---|---|---|---|---|---|---|
| 1 | $CH_3O-$ | $-C_2H_5$ | $-OC_2H_5$ | H | S | 1-N-methoxycarbo-4-N-ethyl,O-ethyl-phosphonodithioylacetyl piperazine | 1.5500 |
| 2 | $CH_3O-$ | $-C_2H_5$ | $-OC_3H_7-i$ | H | S | 1-N-methoxycarbo-4-N-ethyl,O-i-propylphosphonodithioylacetyl piperazine | 1.5424 |
| 3 | $CH_3O$ | $-OC_2H_5$ | $-OC_2H_5$ | H | S | 1-N-methoxycarbo-4-N-O,O-diethyl-phosphorodithioylacetyl piperazine | 1.5340 |
| 4 | $C_2H_5O-$ | $-C_2H_5$ | $-OC_2H_5$ | H | S | 1-N-ethoxycarbo-4-N-ethyl,O-ethyl-phosphonodithioylacetyl piperazine | 1.5414 |
| 5 | $C_2H_5O-$ | $-C_2H_5$ | $-OC_2H_5$ | $CH_3$ | S | 1-N-ethoxycarbo-4-N'-ethyl,O-ethyl-phosphonodithioylacetyl-3-methyl piperazine | 1.5365 |
| 6 | $C_2H_5O-$ | $-C_2H_5$ | $-OC_3H_7-i$ | H | S | 1-N-ethoxycarbo-4-N-ethyl,O-iso-propylphosphonodithioylacetyl piperazine | 1.5350 |
| 7 | $C_2H_5O-$ | $-C_2H_5$ | $-OC_3H_7-i$ | $CH_3$ | S | 1-N-ethoxycarbo-4-N'-ethyl,O-iso propylphosphonodithioylacetyl-3-methyl piperazine | 1.5293 |
| 8 | $C_2H_5O-$ | $-C_2H_5$ | $-OC_4H_9-i$ | H | S | 1-N-ethoxycarbo-4-N-ethyl,O-i-butyl phosphonodithioylacetyl piperazine | 1.5291 |
| 9 | $C_2H_5O-$ | $-C_2H_5$ | $-OC_4H_9-i$ | $CH_3$ | S | 1-N-ethoxycarbo-4-N'-ethyl,O-iso-butylphosphonodithioylacetyl-3-methyl piperazine | 1.5295 |
| 10 | $C_2H_5O-$ | $-OCH_3$ | $-OCH_3$ | H | S | 1-N-ethoxycarbo-4-N-O,O-dimethyl-phosphorodithioylacetyl piperazine | 1.5416 |
| 11 | $C_2H_5O-$ | $-OCH_3$ | $-OCH_3$ | $CH_3$ | S | 1-N-ethoxycarbo-4-N'-O,O-dimethyl-phosphorodithioylacetyl-3-methyl piperazine | 1.5361 |
| 12 | $C_2H_5O-$ | $-OC_2H_5$ | $-OC_2H_5$ | H | S | 1-N-ethoxycarbo-4-N-O,O-diethyl-phosphorodithioylacetyl piperazine | 1.5300 |
| 13 | $C_2H_5O-$ | $-OC_2H_5$ | $-OC_2H_5$ | $CH_3$ | S | 1-N-ethoxycarbo-4-N'-O,O-diethyl-phosphorodithioylacetyl-3-methyl piperazine | 1.5255 |
| 14 | $C_2H_5O-$ | $-OC_2H_5$ | $-OC_2H_5$ | $CH_3$ | O | 1-N-carboethoxy-4-N'-O,O-diethyl-phosphoromonothioylacetyl-3-methyl piperazine | 1.5015 |

TABLE I-continued
PIPERAZINE PHOSPHATES AND PHOSPHONATES

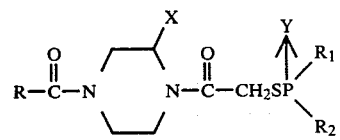

| Compound No. | R | $R_1$ | $R_2$ | X | Y | Chemical Name | Refractive Index |
|---|---|---|---|---|---|---|---|
| 15 | i-$C_3H_7O$— | —$C_2H_5$ | —$OC_2H_5$ | H | S | 1-N-isopropoxycarbo-4-N-ethyl,O-ethylphosphonodithioylacetyl piperazine | 1.5405 |
| 16 | i-$C_3H_7O$— | —$C_2H_5$ | —$OC_3H_7$—i | H | S | 1-N-isopropoxycarbo-4-N-ethyl,O-isopropylphosphonodithioylacetyl piperazine | 1.5320 |
| 17 | i-$C_3H_7O$— | —$C_2H_5$ | —$OC_4H_9$—i | H | S | 1-N-isopropoxycarbo-4-N-ethyl,O-isobutylphosphonodithioylacetyl piperazine | 1.5305 |
| 18 | i-$C_3H_7O$— | —$OCH_3$ | —$OCH_3$ | H | S | 1-N-ispropoxycarbo-4-N-O,O-dimethylphosphorodithioylacetyl piperazine | 1.5375 |
| 19 | i-$C_3H_7O$— | —$OC_2H_5$ | —$OC_2H_5$ | H | S | 1-N-isopropoxycarbo-4-N-O,O-diethylphosphorodithioylacetyl piperazine | 1.5255 |
| 20 | i-$C_3H_7O$— | —$OC_2H_5$ | —$OC_2H_5$ | H | O | 1-N-isopropoxycarbo-4-N-O,O-diethylphosphoromonothioylacetyl piperazine | 1.4990 |
| 21 | $C_6H_5O$— | —$C_2H_5$ | —$OC_2H_5$ | H | S | 1-N-phenyloxycarbo-4-N-ethyl,O-ethylphosphonodithioylacetyl piperazine | 1.5714 |
| 22 | $C_6H_5O$— | —$C_2H_5$ | —$OC_3H_7$—i | H | S | 1-N-phenyloxycarbo-4-N-ethyl,O-isopropyldithioylacetyl piperazine | 1.5625 |
| 23 | $C_6H_5O$— | —$OC_2H_5$ | —$OC_2H_5$ | H | S | 1-N-phenyloxycarbo-4-N-O,O-diethylphosphorodithioylacetyl piperazine | 1.5602 |
| 24 | $CH_3S$— | —$C_2H_5$ | —$OC_2H_5$ | H | S | 1-N-methylthiocarbo-4-N-ethyl,O-ethylphosphonodithioylacetyl piperazine | 1.5740 |
| 25 | $CH_3S$— | —$C_2H_5$ | —$OC_4H_9$—i | H | S | 1-N-methylthiocarbo-4-N-ethyl,O-isobutylphosphonodithioylacetyl piperazine | 1.5607 |
| 26 | $CH_3O$— | $OCH_3$ | —$OCH_3$ | H | S | 1-N-methylthiocarbo-4-N-O,O-di methylphosphorodithioylacetyl piperazine | 1.5760 |
| 27 | $CH_3S$— | —$OC_2H_5$ | —$OC_2H_5$ | H | S | 1-N-methylthiocarbo-4-N-O,O-di-ethylphosphorodithioylacetyl piperazine | 1.5605 |
| 28 | $CH_3S$— | —$OC_2H_5$ | —$OC_2H_5$ | H | O | 1-N-methylthiocarbo-4-N-O,O-diethylphosphoromonothioylacetyl piperazine | 1.5360 |
| 29 | $(CH_3)_3CS$— | —$C_2H_5$ | —$OC_2H_5$ | $CH_3$ | S | 1-N-carbo-t-butylthio-4-N'-ethyl,O-ethylphosphonodithioylacetyl-3-methyl piperazine | 1.5535 |
| 30 | $(CH_3)_3CS$— | —$C_2H_5$ | —$OC_3H_7$—i | $CH_3$ | S | 1-N-carbo-t-butylthio-4-N'-ethyl,O-isopropylphosphonodithioylacetyl-3-methyl piperazine | 1.5426 |
| 31 | $(CH_3)_3CS$— | —$C_2H_5$ | —$OC_4H_9$—i | $CH_3$ | S | 1-N-carbo-t-butylthio-4-N'-ethyl,O-isobutylphosphonodithioylacetyl-3-methyl piperazine | 1.5400 |
| 32 | $(CH_3)_3CS$— | —$OCH_3$ | —$OCH_3$ | $CH_3$ | S | 1-N-carbo-t-butylthio-4-N'-O,O-dimethylphosphorodithioylacetyl- | 1.5454 |

TABLE I-continued

PIPERAZINE PHOSPHATES AND PHOSPHONATES

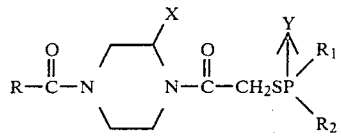

| Compound No. | R | $R_1$ | $R_2$ | X | Y | Chemical Name | Refractive Index |
|---|---|---|---|---|---|---|---|
| | | | | | | 3-methyl piperazine | |
| 33 | $(CH_3)_3CS-$ | $-OC_2H_5$ | $-OC_2H_5$ | $CH_3$ | S | 1-N-carbo-t-butylthio-4-N'-O,O-diethylphosphorodithioylacetyl-3-methyl piperazine | 1.5418 |

Insecticidal and Miticidal Evaluation

The term "insect" is used herein broadly to describe not only six-legged winged species of the insecta class, but also wingless arthropods having more than six legs.

Screening was initiated at a maximal concentration level believed to be injurious to the insect population. The initial level should not be understood as representing a maximum at which a viable test for insecticidal activity can be conducted. Concentrations of the test compounds were successively diluted to levels necessary to obtain 50% mortality ($LD_{50}$) of the treated insect population.

Mobile insects, such as houseflies, German cockroaches, Lygus bugs, were contained for treatment in circular cardboard cages covered with cellophane on the bottom and tulle netting on the top.

The insecticidal and miticidal properties of the compounds of Table I were tested on the following species.

Housefly [*Musca domestica* (Linn.)], (HF)—Contact Residue Assay

Test compounds were diluted in acetone and aliquots were pipetted onto the bottom of 55×15 millimeter (mm) aluminum dishes. One ml of acetone containing 0.02% peanut oil was added to each dish to insure even spreading. After all solvents had evaporated the dishes were placed in cages each containing 25 one to two day old female houseflies. Each cage contained a sugar-water cotton plug for sustanence of the flies.

Mortality rates were recorded after 48 hours. Test levels ranged from 10 μ/25 ♀ houseflies down to that at which approximately 50% mortality occurs. Black Bean Aphid [*Aphis fabae* (Scop.)], (BBA)

Nasturtium plants, *Tropaeolum sp.*, approximately five centimeters (cm) high were transplanted into sandy loam soil in three-inch clay pots. Each pot was infested with 25–50 black bean aphids of mixed ages. Twenty-four hours later the pots were sprayed to the point of run-off with 50—50 acetone-water solutions of the test compounds.

Mortality rates were recorded after the infested plants had been held in the greenhouse for three days. Test concentrations ranged from 0.05% down to that at which 50% mortality occurs. Green Peach Aphid [*Myzus persicae* (Sulzer)], (GPA)

The insecticidal properties were tested in the same manner as for black beam aphids with the substitution of the nasturtiums by radish plants, Rhaphanus sativus. German Cockroach [*Blatella germanica* (Linne)], (GR)—Direct Spray Test compounds were diluted in a 50—50 acetonewater solution. Two cubic centimeters (cc) of the compound solutions were sprayed through a DeVilbiss type EGA hand spray gun into cages each containing 10 one-month-old German cockroach nymphs.

The percent mortality was recorded 7 days later. Test concentrations ranged from 0.1% down to that at which approximately 50% mortality occurs.

Lygus Bug [*Lygus hesperus* (Knight)], (LB)—Direct Spray Assay

The species was treated in the same manner as the German cockroach. The cages contained one string beam pod and 10 adult Lygus bugs. The percent mortality was recorded 48 hours later. Test concentrations ranged from 0.05% down to that at which approximately 50% mortality occurs. Saltmarsh Caterpillar [*Estigmene acrea* (Drury)], (SMC)—Leaf Dip Assay Test compounds were diluted in a 50—50 acetone-water solution. Approximately 1×1.5 inch sections of curly dock (*Rumex crispus*) leaves were immersed in the test solution for 2–3 seconds. After drying on a wire screen, the leaves were placed in petri dishes containing a moistened piece of filter paper. Each dish was infested with 5 secondinstar saltmarsh larvae.

Mortality of the larvae was recorded 48 hours later. A piece of synthetic media was added to the dishes containing surviving larvae. The larvae were then observed for 5 additional days for delayed effects of the test compounds. Test concentrations ranged from 0.05% down to that at which approximately 50% mortality occurs. Cabbage Looper [*Trichoplusia ni* (Hubner)], (CL)

The effectiveness of the compounds was tested in the same manner as for the saltmarsh caterpillar with two exceptions. Cotyledons of hyzini squash (*Calabacita abobrinha*, were substituted for curly dock leaves and the initial test concentration was 0.1%. Tobacco Budworm [*Heliothis virescens* (Fabricius)], (TBW)

Tobacco budworms were tested in the same manner as the cabbage looper. Romaine lettuce (*Latuca sativa*) leaves provided the substrate. Southern House Mosquito Larvae (*Culex pipiens quinquefasciatus*), (M)

Ten third-instar larvae were placed in a six ounce wax paper cup containing 100 ml of an aqueous solution of the test compounds at a concentration of 1 ppm. The treated larvae were stored at 70° F. (21.5° C.) and mortality was recorded 48 hours after treatment. Two-Spotted Mite [*Tetranychus urticae* (Koch)], (2SM)

Pinto bean plants (*Phaseolus vulgaris*) approximately 10 cm high were transplanted into sandy loam soil in three-inch clay pots. The plants were thoroughly infested with two-spotted mites of mixed ages and sexes.

Twenty-four hours after infestation the plants were inverted and dipped for 2-3 seconds in 50—50 acetone-water solutions of the test compounds.

Mortality ratings for both adult mites and nymphs hatching after treatment were taken seven days later. Test concentrations ranged from 0.05% down to that at which 50% mortality occurs.

The results of these tests are reported in Table II. A less than 50% mortality rate at the initial concentration is indicated by a "greater than" sign (>). An approximately 50% mortality rate is indicated by the initial concentration rate. Other results are the dilutions at which an $LD_{50}$ was achieved.

| KEY TO TABLE II | |
|---|---|
| HF | housefly |
| BBA | black bean aphid |
| GPA | green peach aphid |
| GR | German cockroach |
| LB | Lygus bug |
| SMC | saltmarsh caterpillar |
| CL | cabbage looper |
| TBW | tobacco budworm |
| M | mosquito |
| 2SM | two-spotted mite |
| > = greater than | |
| < = less than | |
| — = not tested | |

It is possible to use a 100% pure compound or highly concentrated liquid for application by atomizing equipment, such as aerial spraying.

Generally, the compounds are formulated with one or more inert carriers or diluents. Liquid compositions, such as emulsions, solutions, suspensions, emulsifiable concentrates and pastes, may additionally contain: surface-active wetting, dispersing, and emulsifying agents; solvents; adhesives; thickeners; binders; and anti-foaming agents.

Compositions generally contain from 5 to 95% active ingredient and preferably contain 10 to 85% active ingredient.

Wettable powders and pastes are obtained by mixing and grinding an active compound with one or more dispersing agents, such as lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, e.g., butanol, cyclohexane, xylenes, or higher boiling aromatic hydrocarbons. To obtain suspensions or emulsions in water, wetting agents are also added.

Solid formulations include dusts, granules, tablets, powders and the like. Solid carriers or diluents include: ground natural minerals, e.g., kaolins, alumina, calcium carbonate, silica, kieselguhr, clay, etc.; ground synthetic minerals, e.g., silicates and alumina-silicates; and ground vegetable products, e.g., bark, cornmeal, sawdust, cellulose powder and the like.

Granules may be manufactured by dissolving an active compound in an organic solvent and applying the mixture by atomization onto an absorptive granulated

TABLE II

Insecticidal and Miticidal Effectiveness

| Compound No. | HF μg/25 | BBA % | GPA % | GR % | LB % | SMC % | CL % | TBW % | M ppm | 2SM Adults % | 2SM Eggs % |
|---|---|---|---|---|---|---|---|---|---|---|---|
| 1 | >10 | .0008 | .002 | >.1 | .05 | — | >.1 | >.1 | 1 | .002 | .01 |
| 2 | >10 | .0005 | .001 | >.1 | >.05 | — | >.1 | >.1 | 1 | .001 | .002 |
| 3 | >10 | .001 | .01 | >.1 | >.05 | — | >.1 | >.1 | >1 | <.05 | <.05 |
| 4 | >10 | .0002 | .002 | >.1 | >.05 | .01 | .1 | >.1 | 1 | .003 | .01 |
| 5 | >10 | .0002 | .003 | >.1 | >.05 | >.005 | >.1 | .1 | >1 | <.05 | <.05 |
| 6 | >10 | .0002 | .003 | <.1 | >.05 | .05 | .1 | >.1 | .5 | .001 | .002 |
| 7 | >10 | >.005 | — | — | — | .05 | — | — | .04 | <.05 | <.05 |
| 8 | >10 | .0002 | .003 | <.1 | >.05 | <.05 | .02 | .02 | .3 | <.05 | <.05 |
| 9 | >10 | .0005 | .001 | .07 | .04 | <.05 | .007 | .03 | .05 | <.05 | <.05 |
| 10 | >10 | .0002 | .002 | >.1 | >.05 | — | >.1 | >.05 | 1 | .002 | .005 |
| 11 | >10 | .002 | .03 | >.1 | >.05 | .05 | >.1 | .1 | 1 | <.05 | <.05 |
| 12 | >10 | .001 | .008 | >.1 | >.05 | >.05 | >.1 | >.1 | >1 | .001 | .002 |
| 13 | >10 | .003 | .008 | >.1 | >.05 | >.05 | >.1 | >.05 | >1 | .003 | .006 |
| 14 | >10 | .0005 | .005 | >.1 | >.05 | >.005 | >.1 | >.1 | >1 | <.05 | <.05 |
| 15 | >10 | .003 | .002 | >.1 | >.05 | .01 | >.1 | >.1 | >1 | <.05 | <.05 |
| 16 | >10 | .0002 | .001 | >.1 | >.05 | — | .1 | >.1 | >1 | >.05 | <.05 |
| 17 | >10 | .005 | .003 | >.1 | — | .02 | — | >.1 | .2 | <.05 | <.05 |
| 18 | >10 | .0005 | .005 | >.1 | >.05 | >.05 | >.1 | >.1 | 1 | <.05 | <.05 |
| 19 | >10 | .0006 | .006 | >.1 | >.05 | >.05 | >.1 | >.1 | >1 | <.05 | <.05 |
| 20 | >10 | .0005 | .008 | >.1 | >.05 | >.05 | >.1 | .1 | >1 | <.05 | <.05 |
| 21 | >10 | .002 | .003 | >.1 | >.05 | >.05 | .03 | >.1 | .4 | <.05 | <.05 |
| 22 | >10 | .0001 | .002 | >.1 | .05 | .03 | .01 | >.05 | .8 | <.05 | <.05 |
| 23 | >10 | .002 | .008 | >.1 | >.05 | — | .1 | >.1 | 1 | <.05 | <.05 |
| 24 | >10 | .002 | .002 | >.1 | >.05 | — | .1 | >.1 | .8 | .003 | .005 |
| 25 | >10 | .0005 | .002 | >.1 | >.05 | .03 | .008 | .1 | .2 | <.05 | <.05 |
| 26 | >10 | .0008 | .005 | >.1 | >.05 | .03 | >.1 | >.05 | >1 | >.05 | >.05 |
| 27 | >10 | .001 | .01 | >.1 | >.05 | — | >.1 | >.1 | >1 | <.05 | <.05 |
| 28 | >10 | .0002 | .008 | >.1 | >.05 | >.05 | >.1 | >.1 | >1 | <.05 | <.05 |
| 29 | >10 | >.005 | — | — | — | — | — | >.05 | .8 | — | — |
| 30 | >10 | .0008 | .008 | >.1 | .05 | .02 | .1 | >.05 | .8 | >.05 | >.05 |
| 31 | >10 | .005 | .03 | >.1 | .03 | .02 | .006 | >.05 | .2 | >.05 | >.05 |
| 32 | >10 | >.05 | — | — | — | — | — | >.05 | >1 | >.05 | >.05 |
| 33 | >10 | >.005 | — | — | — | — | — | >.05 | — | — | — |

Formulations

The compounds of this invention are generally formulated into a form suitable for convenient application.

inert material. Adhesives may be utilized for incorporation of the compounds onto the solid particles.

Formulations may also contain other active pesticidal agents, such as herbicides, fungicides, insecticides, acaricides, nematocides, bactericides, and plant growth regulators.

Multi-purpose compositions may additionally contain soil disinfectants, fumigants, and fertilizers.

Insecticidal control may be achieved by direct application of the active compound to the insect. It may be accomplished indirectly by application to insect food sources and habitats.

It should be noted that the active compounds need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (after infestation). Thus, powders and various liquid compositions containing the active compound can be applied by the use of power dusters, boom and hand-sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions applied to the surface of the soil can be distributed below the surface of the soil by conventional means such as discing or mixing operations.

I claim:

1. A compound having the formula

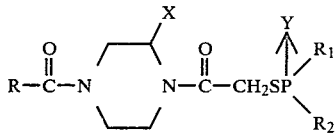

in which
R is selected from the group consisting of 1–4 carbon alkoxy, phenyloxy and 1–6 carbon alkylthio;
$R_1$ is selected from the group consisting of 1–4 carbon alkyl and 1–4 carbon alkoxy;
$R_2$ is 1–6 carbon alkoxy;
X is hydrogen or methyl; and
Y is sulfur or oxygen.

2. A compound according to claim 1 in which R is methoxy, $R_1$ is ethyl, $R_2$ is alkoxy, X is hydrogen and Y is sulfur.

3. A compound according to claim 2 in which $R_2$ is ethoxy.

4. A compound according to claim 2 in which $R_2$ is i-propoxy.

5. A compound according to claim 1 in which R is ethoxy, $R_1$ is ethyl, $R_2$ is alkoxy, X is hydrogen, and Y is sulfur.

6. A compound according to claim 5 in which $R_2$ is ethoxy.

7. A compound according to claim 5 in which $R_2$ is i-propoxy.

8. A compound according to claim 5 in which $R_2$ is i-butoxy.

9. A compound according to claim 1 in which R is ethoxy, $R_1$ is ethyl, $R_2$ is alkoxy, X is methyl, and Y is sulfur.

10. A compound according to claim 9 in which $R_2$ is ethoxy.

11. A compound according to claim 9 in which $R_2$ is i-butoxy.

12. A compound according to claim 1 in which R is ethoxy, $R_1$ and $R_2$ are each methoxy, X is hydrogen, and Y is sulfur.

13. A compound according to claim 1 in which R is ethoxy, $R_1$ and $R_2$ are each ethoxy, X is methyl, and Y is oxygen.

14. A compound according to claim 1 in which R is i-propoxy, $R_1$ is ethyl, $R_2$ is i-propoxy, X is hydrogen and Y is sulfur.

15. A compound according to claim 1 in which R is i-propoxy, $R_1$ and $R_2$ are each methoxy, X is hydrogen and Y is sulfur.

16. A compound according to claim 1 in which R is i-propoxy, $R_1$ and $R_2$ are each ethoxy, X is hydrogen, and Y is sulfur.

17. A compound according to claim 1 in which R is i-propoxy, $R_1$ and $R_2$ are each ethoxy, X is hydrogen and Y is oxygen.

18. A compound according to claim 1 in which R is phenyloxy, $R_1$ is ethyl, $R_2$ is i-propoxy, X is hydrogen and Y is sulfur.

19. A compound according to claim 1 in which R is methylthio, X is hydrogen, and Y is sulfur.

20. A compound according to claim 19 in which $R_1$ is ethyl, and $R_2$ is i-butoxy.

21. A compound according to claim 19 in which $R_1$ and $R_2$ are each methoxy.

22. A compound according to claim 19 in which $R_1$ and $R_2$ are each ethoxy.

23. A compound according to claim 1 in which R is methylthio, $R_1$ and $R_2$ are each ethoxy, X is hydrogen, and Y is oxygen.

24. A compound according to claim 1 in which R is t-butylthio, $R_1$ is ethyl, $R_2$ is i-butoxy, X is methyl, and Y is sulfur.

25. An insecticidal or miticidal composition of matter comprising:

(a) an insecticidally or miticidally effective amount of a compound having the formula

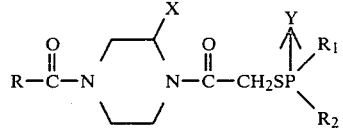

in which
R is selected from the group consisting of 1–4 carbon alkoxy, phenyloxy, and 1–6 carbon alkylthio;
$R_1$ is selected from the group consisting of 1–4 carbon alkyl, and 1–4 carbon alkoxy;
$R_2$ is 1–6 carbon alkoxy;
X is hydrogen or methyl; and
Y is sulfur or oxygen; and (b) an inert carrier or diluent.

26. A method of controlling insects or mites which comprises applying to the insects or mites or the locus thereof an insecticidally or miticidally effective amount of a compound having the formula

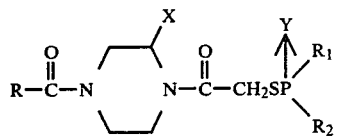

in which
R is selected from the group consisting of 1–4 carbon alkoxy, phenyloxy, and 1–6 carbon alkylthio;
$R_1$ is selected from the group consisting of 1–4 carbon alkyl, and 1–4 carbon alkoxy;
$R_2$ is 1–6 carbon alkoxy;
X is hydrogen or methyl; and
Y is sulfur or oxygen.

27. A method according to claim 26 in which R is methoxy, $R_1$ is ethyl, $R_2$ is alkoxy, X is hydrogen and Y is sulfur.

28. A method according to claim 27 in which $R_2$ is ethoxy.

29. A method according to claim 27 in which $R_2$ is i-propoxy.

30. A method according to claim 26 in which R is ethoxy, $R_1$ is ethyl, $R_2$ is alkoxy, X is hydrogen, and Y is sulfur.

31. A method according to claim 30 in which $R_2$ is ethoxy.

32. A method according to claim 30 in which $R_2$ is i-propoxy.

33. A method according to claim 30 in which $R_2$ is i-butoxy.

34. A method according to claim 26 in which R is ethoxy, $R_1$ is ethyl, $R_2$ is alkoxy, X is methyl, and Y is sulfur.

35. A method according to claim 34 in which $R_2$ is ethoxy.

36. A method according to claim 34 in which $R_2$ is i-butoxy.

37. A method according to claim 26 in which R is ethoxy, $R_1$ and $R_2$ are each methoxy, X is hydrogen, and Y is sulfur.

38. A method according to claim 26 in which R is ethoxy, $R_1$ and $R_2$ are each ethoxy, X is methyl, and Y is oxygen.

39. A method according to claim 26 in which R is i-propoxy, $R_1$ is ethyl, $R_2$ is i-propoxy, X is hydrogen and Y is sulfur.

40. A method according to claim 26 in which R is i-propoxy, $R_1$ and $R_2$ are each methoxy, X is hydrogen, and Y is sulfur.

41. A method according to claim 26 in which R is i-propoxy, $R_1$ and $R_2$ are each ethoxy, X is hydrogen, and Y is sulfur.

42. A method according to claim 26 in which R is i-propoxy, $R_1$ and $R_2$ are each ethoxy, X is hydrogen, and Y is oxygen.

43. A method according to claim 26 in which R is phenyloxy, $R_1$ is ethyl, $R_2$ is i-propoxy, X is hydrogen, and Y is sulfur.

44. A method according to claim 26 in which R is methylthio, X is hydrogen and Y is sulfur.

45. A method according to claim 44 in which $R_1$ is ethyl, and $R_2$ is i-butoxy.

46. A method according to claim 44 in which $R_1$ and $R_2$ are each methoxy.

47. A method according to claim 44 in which $R_1$ and $R_2$ are each ethoxy.

48. A method according to claim 26 in which R is methylthio, $R_1$ and $R_2$ are each ethoxy, X is hydrogen, and Y is oxygen.

49. A method according to claim 26 in which R is t-butylthio, $R_1$ is ethyl, $R_2$ is i-butoxy, X is methyl, and Y is sulfur.

* * * * *

UNITED STATES PATENT AND TRADEMARK OFFICE
CERTIFICATE OF CORRECTION

PATENT NO. : 4,225,595
DATED : September 30, 1980
INVENTOR(S) : Llewellyn W. Fancher It is certified that error appears in the above—identified patent and that said Letters Patent is hereby corrected as shown below:

Column 2, Example 1, line 8, please change ...3.52 grams (g) or 0.015 mole)... to read ---(3.52 grams (g) or 0.015 mole)---.

Column 7, line 48, please change ...10 μ/25... to read ---10 μg/25---.

Column 7, lines 49 & 50, please delete the sentence "Black Bean Aphid..." from that paragraph. "Black Bean Aphid [Aphis fabae (Scop.)], (BBA)" should be the side-heading for the paragraph "Nasturtium plants...".

UNITED STATES PATENT AND TRADEMARK OFFICE
CERTIFICATE OF CORRECTION

PATENT NO. : 4,225,595

DATED : September 30, 1980

INVENTOR(S) : Llewellyn W. Fancher

It is certified that error appears in the above—identified patent and that said Letters Patent is hereby corrected as shown below:

Column 7, lines 61 & 62, please delete the sentence "Green Peach Aphid..." from that paragraph. "Green Peach Aphid [Myzus persicae (Sulzer)], (GPA)" should be the side-heading for the paragraph starting with "The insecticidal...".

Column 7, line 64, please change the word ...beam...to read ---bean---.

Column 8, line 30, please change the word ...beam... to read ---bean---.

Column 8, lines 33 & 34 please delete the sentence "Saltmarsh Caterpillar..." from that paragraph. "Saltmarsh Caterpillar [Estigmene acrea (Drury)], (SMC)-Leaf Dip Assay" should be the side-heading for the paragraph starting with "Test compounds were---".

Column 8, line 41, please change ...secondinstar... to read ---second-instar---.

Column 8, lines 48 & 49, please delete the last sentence "Cabbage Looper..." from that paragraph. "Cabbage Looper [Trichoplusia ni (Hubner)], (CL)" should be the side-heading for the paragraph starting with "The effectiveness---".

Column 8, lines 54 & 55, please delete the last sentence "Tobacco Budworm..." from that paragraph. "Tobacco Budword [Heliothis virescens (Fabricius)], (TBW)" should be the side-heading for the paragraph starting with "Tobacco budworms were tested---."

UNITED STATES PATENT AND TRADEMARK OFFICE
CERTIFICATE OF CORRECTION

PATENT NO. : 4,225,595

DATED : September 30, 1980

INVENTOR(S) : Llewellyn W. Fancher

It is certified that error appears in the above—identified patent and that said Letters Patent is hereby corrected as shown below:

Column 8, lines 58 & 59, please delete the last sentence "Southern House Mosquito..." from that paragraph. "Southern House Mosquito Larvae (Culex pipiens quinquefasciatus), (M)" should be the side-heading for the paragraph starting with "Ten third-instar---."

Column 8, lines 64 & 65, please delete the last sentence "Two-Spotted Mite..." from that paragraph. "Two-Spotted Mite [Tetranychus urticae (Koch)], (2SM)" should be the side-heading for the paragraph starting with "Pinto bean plant...".

Table II, Compound 8, under the heading "GR", please change "$<.1$" to read -- "$>.1$"--.

Signed and Sealed this

First Day of December 1981

[SEAL]

Attest:

GERALD J. MOSSINGHOFF

Attesting Officer  Commissioner of Patents and Trademarks